United States Patent
McNabb

(10) Patent No.: US 7,904,285 B2
(45) Date of Patent: Mar. 8, 2011

(54) METHOD, SYSTEM AND APPARATUS FOR ACCESSING, MODULATING, EVOKING, AND ENTRAINING GLOBAL BIO-NETWORK INFLUENCES FOR OPTIMIZED SELF-ORGANIZING ADAPTIVE CAPACITIES

(76) Inventor: Gary McNabb, Eugene, OR (US)

( * ) Notice: Subject to any disclaimer, the term of this patent is extended or adjusted under 35 U.S.C. 154(b) by 86 days.

(21) Appl. No.: 11/478,732

(22) Filed: Jul. 3, 2006

(65) Prior Publication Data

US 2007/0016096 A1 Jan. 18, 2007

Related U.S. Application Data

(60) Provisional application No. 60/695,418, filed on Jul. 1, 2005.

(51) Int. Cl.
*G06G 7/58* (2006.01)
*G01N 33/48* (2006.01)
*G06F 7/60* (2006.01)

(52) U.S. Cl. ............... 703/11; 702/19; 702/20; 703/2; 700/90

(58) Field of Classification Search ............... 600/300, 600/301; 128/903–905, 920
See application file for complete search history.

(56) References Cited

U.S. PATENT DOCUMENTS

| | | | |
|---|---|---|---|
| 4,461,301 A | 7/1984 | Ochs | 128/630 |
| 4,571,682 A | 2/1986 | Silverman et al. | 364/413 |
| 4,928,704 A | 5/1990 | Hardt | 128/732 |
| 5,163,690 A | 11/1992 | Davis et al. | 273/460 |
| 5,209,494 A | 5/1993 | Spector | 273/460 |
| 5,213,338 A | 5/1993 | Brotz | 273/460 |
| 5,253,168 A | 10/1993 | Berg | 364/413.01 |
| 5,377,100 A | 12/1994 | Pope et al. | 364/410 |
| 5,450,855 A | 9/1995 | Rosenfeld | 128/732 |
| 5,546,943 A | 8/1996 | Gould | 128/653.1 |
| 5,678,571 A | 10/1997 | Brown | 128/898 |
| 5,720,619 A | 2/1998 | Fisslinger | 434/336 |
| 5,740,812 A | 4/1998 | Cowan | 128/732 |
| 5,741,217 A | 4/1998 | Gero | 600/547 |
| 5,743,744 A | 4/1998 | Cassily et al. | 434/258 |
| 5,911,581 A | 6/1999 | Reynolds et al. | 434/236 |
| 5,995,857 A | 11/1999 | Toomim et al. | 600/322 |
| 6,001,065 A | 12/1999 | DeVito | 600/544 |
| 6,024,700 A | 2/2000 | Nemirovski et al. | 600/300 |
| 6,036,496 A | 3/2000 | Miller et al. | 434/156 |
| 6,057,846 A | 5/2000 | Sever, Jr. | 345/419 |
| 6,067,468 A | 5/2000 | Korenman et al. | 600/547 |
| 6,097,981 A | 8/2000 | Freer | 600/545 |
| 6,168,562 B1 | 1/2001 | Miller et al. | 600/300 |
| 6,172,941 B1 | 1/2001 | Bieramperl | 368/10 |
| 6,190,173 B1 | 2/2001 | Jenkins et al. | 434/169 |
| 6,231,344 B1 * | 5/2001 | Merzenich et al. | 434/236 |
| 6,280,198 B1 | 8/2001 | Calhoun et al. | 434/236 |
| 6,306,077 B1 | 10/2001 | Prabhu et al. | 600/26 |
| 6,309,342 B1 | 10/2001 | Blazey et al. | 600/26 |
| 6,334,777 B1 | 1/2002 | Jenkins et al. | 434/185 |
| 6,384,729 B1 | 5/2002 | Plotkin | 340/573.1 |
| 6,402,520 B1 | 6/2002 | Freer | 434/236 |
| 6,425,674 B1 | 7/2002 | Su | 362/629 |
| 6,435,878 B1 | 8/2002 | Reynolds et al. | 434/236 |
| 6,450,820 B1 | 9/2002 | Palsson et al. | 434/236 |
| 6,478,735 B1 | 11/2002 | Pope et al. | 600/300 |
| 6,520,905 B1 | 2/2003 | Surve et al. | 600/26 |
| 6,546,378 B1 | 4/2003 | Cook | 706/12 |
| 6,549,805 B1 | 4/2003 | Nesterov et al. | 600/545 |
| 6,565,359 B2 | 5/2003 | Calhoun et al. | 434/236 |
| 6,579,248 B1 | 6/2003 | Cascone et al. | 600/587 |
| 6,623,427 B2 | 9/2003 | Mandigo | 600/300 |
| 6,626,676 B2 | 9/2003 | Freer | 434/236 |
| 6,634,949 B1 | 10/2003 | Briggs et al. | 463/42 |
| 6,662,032 B1 | 12/2003 | Gavish et al. | 600/323 |
| 6,702,767 B1 | 3/2004 | Douglas et al. | 601/15 |
| 6,774,885 B1 | 8/2004 | Even-Zohar | 345/156 |
| 2002/0128541 A1 | 9/2002 | Kim et al. | 600/301 |
| 2002/0182574 A1 | 12/2002 | Freer | 434/236 |
| 2003/0050537 A1 * | 3/2003 | Wessel | 600/300 |
| 2003/0060728 A1 | 3/2003 | Mandigo | 600/545 |
| 2003/0149676 A1 | 8/2003 | Kasabov | 706/2 |
| 2004/0077934 A1 | 4/2004 | Massad | 600/300 |
| 2004/0092809 A1 | 5/2004 | DeCharms | 600/410 |
| 2004/0138578 A1 | 7/2004 | Pineda et al. | 600/544 |
| 2005/0043894 A1 * | 2/2005 | Fernandez | 702/19 |
| 2005/0124906 A1 | 6/2005 | Childre et al. | 600/529 |

FOREIGN PATENT DOCUMENTS

| | | |
|---|---|---|
| EP | 1146406 A1 | 10/2001 |
| GB | 2405203 | 2/2005 |
| WO | WO 00/09007 | 2/2000 |

* cited by examiner

*Primary Examiner* — Shubo (Joe) Zhou
(74) *Attorney, Agent, or Firm* — Pillsbury Winthrop Shaw Pittman LLP

(57) ABSTRACT

The invention interacts with subjects to query, challenge, and identify aspects and multidimensional influences providing access to, modulation and entrainment of, state-specific global bio-regulatory self-organizing controllers and evocable triggers. Modulating state-specific regulatory triggers may evoke optimized emergent self-organizing principles within a subject and support up-regulating "states of presence," including newly emergent controllers of additional optimal regulation of bio-chemical expressions. A subject's "state" measures may include the status of a combination of multiple identified biological qualities. Provided are systems and methods supporting access to a subject's state controller functions, for various ailments, to empower shifting ones' biology from a symptomatic to an asymptomatic state and to optimal adaptive learning and readiness. Also enabled are investigation and access to capacities that control such state shifts so that they can be broadly challenged, expanded, and entrained for optimized global regulatory function in reversing a myriad of pathological symptoms, learning limitation, and adaptive dysregulations.

27 Claims, 6 Drawing Sheets

US 7,904,285 B2

METHOD, SYSTEM AND APPARATUS FOR ACCESSING, MODULATING, EVOKING, AND ENTRAINING GLOBAL BIO-NETWORK INFLUENCES FOR OPTIMIZED SELF-ORGANIZING ADAPTIVE CAPACITIES

REFERENCE TO RELATED APPLICATIONS

This application claims the benefit of U.S. Provisional Patent Application No. 60/695,418, filed Jul. 1, 2005, which is hereby incorporated herein by reference in its entirety.

FIELD OF THE INVENTION

This invention relates to a system, method, and apparatus for using biofeedback training in conjunction with bio-molecular data and analysis to map, modulate, and entrain optimized self-organizing adaptive capacities in living systems. More, particularly, the invention relates to a system, method, and apparatus for identifying augmenting, and learning-reinforcing near-global and global networked controllers of inherent, self-organizing, bio-adaptive capacities to support adaptive supra-readiness in meeting environmental/life challenges.

BACKGROUND

With the advent of the age of information, and the many emerging insights of systems and co-evolutionary complexity theoretical models, the investigational methods of science, as they especially pertain to education, healthcare, and general optimal performance outcomes, are poised for dramatic improvements. In medical research especially, these new investigational technologies are giving rise to a myriad of new designs for diagnostic equipment, medical devices, and computer-implemented technologies that enable health care professionals to more effectively identify and propose next-generation treatments for numerous human ailments. In education and training contexts, there are similar emerging refinements in biology-based strategies for developing and conveying learning methods and the skillful delivery of content that can be more readily integrated by the brain for optimal utilization and performance.

Traditionally, computer and information technology have been used by health care professionals in several basic ways: to physically interact with patients, to visualize certain areas of the body which were previously inaccessible, or to perform complex computations crucial to patient diagnosis and treatment. However, in recent years computer and information technology have been used to interact with and treat patients in a different manner. An example of the use of computers in the treatment of human ailments is the use of biofeedback for therapeutic "games."

Some therapeutic games treat ailments using interactive devices that help patients visualize and control their own previously involuntary biological attributes. Enhancing such visible access to these biological attributes may be relevant to any number ailments suffered by a patient. For example, see U.S. Pat. No. 4,461,301 to Ochs ("Self Adjusting Bio-Feedback Method and Apparatus"), U.S. Pat. No. 5,377,100 to Pope et al. ("Method of Encouraging Attention by Correlating Video Game Difficulty with Attention Level"), U.S. Pat. No. 5,678,571 to Brown ("Method for Treating Medical Conditions Using a Microprocessor-Based Video Game"), each of which are hereby incorporated by reference herein in their entirety. As such, increasing access to parameters that function to control these attributes may enable new treatment of ailments. Therapeutic games often incorporate visualization of these biological attributes into any number of game formats. These therapeutic biofeedback games have been employed in the treatment of ailments such as attention deficit hyperactivity disorder (ADHD), addiction, learning disabilities, schizophrenia, and various other conditions.

Traditional approaches to science, engineering, learning, medicine, and even biofeedback treatment and training often begin with an investigation into the component parts of a system. Once the component parts of a system have been identified, deconstructed, and analyzed, it is generally assumed that the complete function of the system, and thus, any malfunctions thereof, may be derived from the sum of these parts. This "reductionistic" method of science may prove useful in discerning some basic qualities of a system and solving basic problems therein. However, reductionistic methods and their attendant stimulus-response models are based on a limiting understanding of the core causalities that inform complex and dynamic living systems. There exist qualities that may be discerned and implemented only when the "system-as-a-whole" (i.e., holistic) and the controllers of its synergistic self-organizing regulatory networks are accessed, visualized, and better understood as a functional "context."

The complexity of living relationships responsible for controlling the health of a human being, for instance, may be hidden deep within the expressive patterns of genetic and epigenetic regulatory networks. Developing methods that provide a whole-systems approach and access to these networks and their environmental contexts may be available only through a skillful convergence of real-time-living and virtual combinatorial interactions.

Controller strategies evolved by nature have enabled life on earth to survive for eons, adapting to changes by exhibiting phase transitions resulting in autonomous self-organizing, collective, and co-operative capacities. Solutions to complex medical and educational puzzles, as an example, may lie in the living repository of these most co-evolutionarily conserved genetic co-expression contexts, bio-pathways and the regulatory triggers that promote or silence them. In light of such realizations, there is a need and opportunity to include methods beyond those of reductionistic science, which are exemplified by traditional stimulus-response models of causality.

The present invention co-evolutionarily confirms its optimization measures by the integration of the above-mentioned deeply conserved measurable artifacts of evolution. The invention also provides access to the "states" that inform phase-state transitions operating in dynamic systems such as, for example, the brain.

SUMMARY OF THE INVENTION

The invention solves these and other problems by providing a bio-training system, method, and apparatus for inducing a change in a state of a subject. In one embodiment, the bio-training system of the invention samples subject data from the subject. Part or all of the sampled subject data may be indicative of, or relatable to, a current state of the subject. This subject data may be stored as part of a subject record associated with the subject. One or more challenges intended to change and/or more deeply integrate the state of the subject may then be presented to the subject. Additional subject data may then be sampled.

The additional subject data may be stored as part of the subject record and analyzed to determine any change in the state of the subject. The analysis may compare the pre-challenge subject data to the post-challenge subject data. The analysis may also utilize one or more rules that apply a priori knowledge regarding known relationships between subject states and measured subject data. If no such a priori knowledge is known, the analysis may be used, along with additional data obtained by the iterative process below, to elucidate such a priori knowledge and formulate rules for analysis of further challenge-response iterations.

The analysis may demonstrate an effect of the one or more challenges on the state of the subject. For example, the one or more challenges may have changed the state of the patient or had no discernable effect (as measured by the additional subject data). In one embodiment, any discernable change in the state of the patient may have certain characteristics such as, for example, desirable change, undesirable change, neutral or unknown change, an indication of degree of change in state, or other characteristic. These effects and any associated characteristics may then be stored as part of the subject record.

From the analysis, additional challenges may be formulated. The additional challenges may be formulated based on the effect that the previous challenges had on the state of the subject (as measured by the sampled subject data). For example, if previous challenges had no discernable effect or effected an undesirable change in the subject's state, the rules/a priori knowledge may be updated with this information and different challenges may be formulated and presented to the patient in later iterations. If previous challenges had a desirable effect (e.g., moved the subject's state in a desired direction), the rules/a priori knowledge may be updated with this information and those challenges may be repeated, intensified, or subtly modified to discern what qualities of the challenges were most responsible for the desired change in state.

The newly formulated challenges may then be presented to the subject. Further subject data may then be sampled and analyzed. This process of challenge presentation, subject data sampling, and challenge re-formulation may be repeated in an iterative fashion, as necessary, to change the state of the subject to a desired state (or if no specific desired state has been identified, to elucidate a desired state or investigate correlations between challenges, subject data, and subject states—these correlations adding to the rules/a priori knowledge). Each time the process is repeated, additional data is added to the subject record, the rules/a priori knowledge are modified, and the types of challenges that may successfully move the subject toward the desired state are further elucidated. The type of subject data that best reflects various subject states may also be elucidated by repeated application of the above-described process.

Application of the above-described iterative process to multiple subjects may result in multiple subject records that can be analyzed or mined to elucidate correlations between challenges, subject data, and subject state. These correlations may be used to further update the set of rules/a priori knowledge that are used to identify what challenges may be used to move a subject from one particular state to another particular state. For example, multiple records for subjects having the same pathological state (e.g., autism) may be mined to uncover the types of challenges that moved subjects towards a state exhibiting less pathological symptoms. Data resulting from this data mining may be used in the further understanding/treatment of autism in general and may be used to further formulate challenges for treatment/state change induction for additional subjects suffering from autism.

As used herein a "subject" may include a human, a group of humans, an organization of humans, and/or non-human living systems, which may include plants and animals and plant and animal life systems (e.g., colonies, herds, or other groups of plant's or animals). In one example, a subject may include a human who is suffering from, or requires treatment for, an ailment, condition, disease, or symptom thereof. In still other embodiments, a subject may include information systems, informational processes, virtual/simulated computation of biological systems, and/or other networked applications.

In one embodiment, the computer-implemented interactive biofeedback training system (hereinafter "bio-training system") used in the above-described iterative process may include one or more biofeedback sensor devices and/or one or more data input devices for sampling/gathering subject data. The bio-training system may also include a computer system, one or more databases and a bio-training application for storing and modifying rules/a priori knowledge; for receiving, storing and analyzing subject data; for formulating one or more challenges; maintaining subject records; performing data mining functions; and/or for enabling other features or functions of the invention. The bio-training system may also include one or more challenge presentation devices for presenting one or more challenges to the subject according to the iterative process described above.

In one embodiment, the subject data sampled by the bio-training system may include four categories of data related to a subject: 1) biophysical properties, 2) voluntary action, 3) involuntary action, and 4) genetic and epigenetic data.

Biophysical properties may include physiological attributes, or other measurable biological characteristics of a subject including but not limited to: brainwave activity, galvanic skin activity, other bodily electrical activity, blood pressure, pulse rate, blood gas, body temperature, functional brain attributes, or any physiological value capable of being contemporaneously obtained from a subject. The one or more biofeedback sensor devices of the bio-training system may include any device or system capable of measuring one or more biophysical properties of a subject. Biofeedback sensor devices are known to those skilled in the art. More information regarding biofeedback sensor devices and other information useful in the context of the invention can be found in U.S. Pat. No. 6,172,941 to Bieramperl ("Method to Generate Self-Organizing Processes in Autonomous Mechanisms and Organisms"), U.S. Pat. No. 6,402,520 to Freer ("Electroencephalograph Based Biofeedback System for Improving Learning Skills"), and U.S. Pat. No. 6,662,032 to Gavish et al., ("Interventive-Diagnostic Device"), each of which are hereby incorporated by reference herein in their entirety.

Voluntary actions as subject data may be sampled using the one or more data input devices of the bio-training system. The one or more data input devices of the bio-training system may include for example, a keyboard, mouse, an alphanumeric keypad, a touch screen, a voice recognition device (e.g., microphone and associated software), a camera or other optical input device, or other device capable of receiving voluntary input from a subject. In one example, the subject may enter voluntary action subject data into the bio-training system via the one or more input devices by responding to questions, interacting with games or puzzles, or by performing other voluntary actions. In another example, voluntary action subject data may be entered into the bio-training system via the one or more data input devices by an operator or administrator that is observing the voluntary actions of a subject.

Involuntary actions as subject data may be sampled by the one or more biofeedback sensor devices and/or may be entered into the bio-training system via the one or more data input devices by an operator or administrator that is observing the involuntary actions of the subject. Some examples of involuntary actions that can be used as subject data may include observations regarding body language, facial muscle status, eye movement, or other observable or measurable involuntary indicators.

Genetic or epigenetic data as subject data may refer to sampled data indicative of gene transcription (e.g., DNA to mRNA) or molecular regulation thereof, gene translation (e.g., mRNA to amino acid) or molecular regulation thereof, other gene regulatory action in a subject. Genetic or epigenetic expression data may be obtained using known clinical and molecular biological laboratory techniques. The use of conventional molecular biological laboratory techniques to obtain genetic or epigenetic subject data may involve a lag time between sampling of subject cells and the production of actual genetic or epigenetic subject data useful with the bio-training system. However, heretofore unrealized techniques for faster genetic or epigenetic expression data production may be used with the invention when developed, including those capable of measuring gene expression data in real-time or close to real-time. Additionally, genetic or epigenetic data as subject data may include extrapolations of probable genetic or epigenetic expression based on known or predicted correlations between contemporaneously measurable subject data (e.g., biophysical properties, voluntary action, involuntary action, etc.) and genetic or epigenetic expression.

Furthermore, the bio-training system itself may be used to enhance ability of researchers to make such correlations between subject data measurable in real time and gene or epigenetic expression. For example, the above described iterative process may be performed and the state of a subject may be successfully changed (at least incrementally). At each iteration of the process wherein real-time measurable subject data is sampled, a contemporaneous sample of subject cells may be taken. These cells may be later analyzed using molecular laboratory techniques and the resultant genetic/epigenetic expression data may be correlated to its corresponding subject data sampling interval. This expression data may be added to the subject record and used to further enhance the rules/a priori knowledge regarding the genetic basis of changes in subject states and the subject data measurable in real-time that are indicative of certain gene expression. This knowledge, along with ever-deepening rules/a priori knowledge regarding challenges that induce state changes, challenges can now be specifically designed to alter the gene expression of the subject. Thus, the bio-training system provides access to controllers of gene expression, which provides the ability to change and/or more deeply integrate the state of a patient using a powerful state indicator/controller: gene expression.

As mentioned above, the subject need not be a human being. Some investigation into the controllers of genetic/epigenetic expression using the bio-training system may involve plants and/or animal systems. This enables researchers to take samples cells of all types of subject tissues, including those of vital organs, to measure the expression in tissues that may be most prevalent in state change (this access might not be viable for human patients). As described below, the correlation of evolutionarily conserved gene families may be used to relate the states of plants or animal systems to the states of human beings. Thus, investigation of plant or animal systems using the invention may be quite beneficial in enhancing the rules/a priori that are later used with human subjects. In addition, as described herein, the use of the iterative process of the bio-training system on virtual systems/simulations may also be useful in enhancing the rules/a priori knowledge that are ultimately used with human subjects.

As mentioned above, the bio-training system may include a bio-training application. The bio-training application may include one or more software modules enabling the features and functions of the invention. The bio-training module may include a rules engine for developing, storing, modifying, and applying the rules or a prior knowledge of correlated, subject data, challenges, and subject states.

The bio-training system may also include challenge presentation devices for presenting challenges to a subject in connection with the above-described iterative process. A challenge presentation device may include, for example, a display device (e.g., computer monitor, television monitor, liquid crystal display screen), a sound emitting device (e.g., speaker), a vibration device, an electrode, or other device capable of presenting challenges to a subject.

The "state" of a subject may include the status of a combination of any number of identified biological qualities including, but not limited to: pulse rate, blood pressure, skin electrical conductance, respiration rate, brainwave or other body electrical activity, gene and epigenetic expression levels, pain or discomfort level, pathological symptom level, or other biological qualities. Shifts in measurable state are a common medical treatment modality. For example, in cardio-vascular medicine, a broadly utilized treatment of choice includes "beta-blockers." This pharmacological treatment disrupts the habituation of a "beta" brainwave state in the brain and shifts a subject's entire physiology from that associated with habituated beta brainwave states to reclaim access to other brainwave dynamics, with a reversal of habituated cardio-vascular inhibitions and the alleviation of pathological symptoms.

The message contained in the genome of every organism is self-referring, in that it harbors the instructions necessary for the entire construction and reconstruction of the organism itself by transcription. The iterative processes and analysis of the invention focus on this essential self-organizing adaptive capacity for self-reconstruction as a primary index of system health. These essential adaptive capacities are capable of varying scales of regulation. When down-regulation occurs, the processes that sustain such inhibition can become habituated. It is in such circumstances that optimized function becomes more latent within the subject system and may reach a critical mass of "silence" that supports, in a medical model, the formation and emergence of symptomatic dysfunctions, and in training contexts, sub-optimal outcomes and performance.

In one embodiment, the bio-training system and the iterative process described herein enables access to dynamic global state controller functions of a subject to empower shifting the subject's biology (e.g., genetic/epigenetic expression or other biological aspect) from one of habituated symptom formation, learning dysfunction, and/or performance limitation, to an adaptively optimized state, confirmed by self-organizing correlated indices. The systems and methods of the invention investigates and accesses the capacities that control such state shifts so that they can be broadly challenged and expanded for optimized function of a subject's biology.

With the inclusion and convergence of innovative real-time and virtual interactions, and their informational consequences, the invention may be used to identify, query, and challenge regulatory influences that demonstrate sensitivity to amplification of complex bio-regulatory controllers. The novel amplification of these specific identified regulatory influences includes multiple strategies for the evocation of their most appropriate global network controllers. These meta-controller global systems include the dynamic properties of inherent self-organizing adaptive capacities that underlie and support the emergent capacities for specific regulatory influences. The invention may then index these controller influences/capacities to produce a real-time measure of a subject/living system's functional adaptive readiness. With a novel convergence of real-time and virtual environmental training influences, a primary re-regulating focus of the iterative process of the invention is the "state-of-presence" (i.e. "state") of a subject.

These and other objects, features, and advantages of the invention will be apparent through the detailed description and the drawings attached hereto. It is also to be understood that both the foregoing general description and the following detailed description are exemplary and not restrictive of the scope of the invention.

DETAILED DESCRIPTION

Figure 1A:
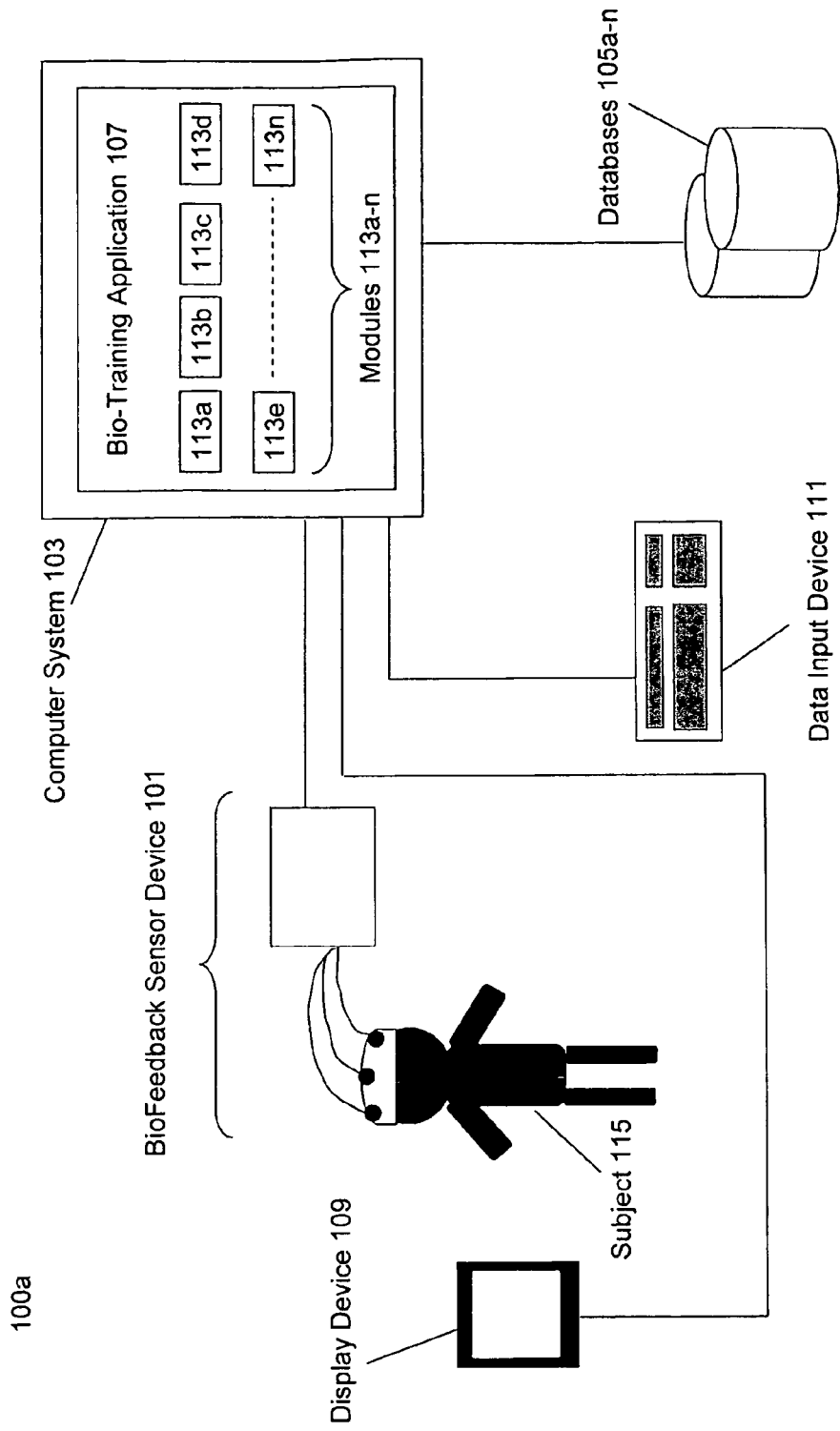
FIG. 1A illustrates a schematic diagram of a bio-training system, according to an embodiment of the invention.

The invention provides a bio-training system, method, and apparatus for inducing and/or more deeply integrating a change in a state of a subject. The invention interacts with a subject (e.g., a human subject) to query, challenge and identify multiple aspects and multidimensional influences that provide access to, and allow modulation of, bio-regulatory controllers/triggers. Modulation of specific bio-regulatory triggers may evoke deeply conserved self-organizing principles within the subject and ultimately support up-regulation of "states of presence" (hereinafter "states") that control optimal bio-chemical (e.g., genetic and epigenetic) expressions and autonomous integration of the skills and learning necessary for optimal readiness. For more information regarding self-organizing principles and cellular biology and other concepts relevant to the invention, see Tom Misteli, *The Concept of Self-Organization in Cellular Architecture*, The Journal of Cell Biology, vol. 155, no. 2, Oct. 15, 2001, pgs 181-186, which is hereby incorporated by reference herein in its entirety. The "state" measures of a person may include the status of a combination of any number of identified biological qualities including, but not limited to: pulse rate, blood pressure, skin electrical conductance, respiration rate, brainwave or other body electrical activity, gene and epigenetic expression levels, pain or discomfort level, pathological symptom level, or other biological quality.

Shifts in measurable state are a common medical treatment modality. For example, in cardiovascular medicine, a broadly utilized treatment of choice includes "beta-blockers." This pharmacological treatment disrupts the habituation of a "beta" brainwave state in the brain and shifts the subject's entire physiology from that associated with habituated beta brainwave states to reclaim access to other brainwave dynamics, with a reversal of habituated cardio-vascular inhibitions and the alleviation of symptoms. In one embodiment, the invention includes a system that supports a subject to re-access appropriate dynamic global state controller functions in the midst of environmental challenges to the subject, for this and many other aliments, to empower shifting ones' biology from one of habituated symptom formation, learning dysfunction, and performance limitation, to an adaptively optimized entrained state, confirmed by self-organizing correlated indices. The system of the invention investigates and accesses the capacities that control such state shifts so that they can be broadly challenged and expanded for optimized entrained function to reduce a myriad of pathological symptoms.

In one embodiment, a bio-training system (e.g., bio-training system 101) may be used to convey and/or suggest various possibilities for shifting the "state" of a subject from one state to a specific desired state. Refining qualities of concentration and presence have a researched history of evoking differing brain states, e.g., beta, alpha, delta, and theta brainwave frequencies. As in the example of improving cardiovascular health by the use of beta-blockers, systematic refinement and integration of brain-altering focus and absorption may be integrated into the bio-training system and may provide a model for exploring systemic aspects of, for instance, lawful molecular bio-chemical influences that support living systems. With the convergence of interactivities and state-specific alteration methodologies, the bio-training system explores state-specific controller influences that shape formative inter-relationships of environmental and genetic and epigenetic expressive influences. The recursive data analysis function of the invention clarifies the lawful roles of these controller influences to identify and model the targeted cellular pathways that give the greatest indication of capacity for state alteration on a state-specific level (e.g., to identify controllable genetic expression patterns that induce specific asymptomatic states).

The synergy of the interactivity function of the bio-training system and the recursive data analysis functions of the bio-training system invention explores mechanisms of action that elucidate evolutionarily conserved regulatory cell-signaling bio-capacities/bio-controllers (hereinafter "bio-controllers") that can be used to control a subject's state. From the elucidated bio-controllers, the bio-training system may explore how these lawful capacities can be engaged to cooperatively to further induce those "states" that support the emergence of adaptations indicating enhanced and/or optimized functional capacities, e.g., neuro-developmental operation (e.g., asymptomatic states).

According to an embodiment of the invention illustrated in FIG. 1A, a system 100a is provided for a computer-implemented interactive biofeedback training system ("bio-training system"). System 100a may include one or more biofeedback sensor devices 101, at least one computer system 103, one or more databases 105a-105n, a bio-training application 107, a data display device 109, a data input device 111, and other components. It should be understood that one or more, computer systems 103, bio-training application 107, or other components of the system of the invention may include various software modules 113a-113n to accomplish the functionalities described herein. In other embodiments, as would be appreciated, the functionalities described herein may be implemented in various combinations of hardware and/or firmware, in addition to, or instead of, software.

Bio-training system 100a may be connected to or otherwise be enabled to interact with, sample data from, or receive data related a subject 115. In some embodiments, subject 115 may include a human, a group of humans, or an organization of humans, and/or non-human living system, which may include plants, animals, and plant and/or animal life systems (e.g., colonies, herds, or other groups of plant's or animals). In one example, subject 115 may include a human who is suffering from, or requires treatment for, an ailment, condition, disease, or symptom thereof. In still other embodiments, subject 115 may include information systems, informational processes, virtual/simulated computation or biological systems, and/or other networked applications.

One or more biofeedback sensor devices 101 may include any device or system capable of measuring and/or recording one or more biophysical properties or physiological attributes (hereinafter referred to as "biophysical properties"). A biophysical property may include but is not limited to: brainwave activity, galvanic skin activity, other bodily electrical activity, blood pressure, pulse rate, blood gas, body temperature, functional brain attributes, or any physiological value capable of being contemporaneously obtained from a subject. Many types of biofeedback sensor devices are known in the art such as, for example; electroencephalographic devices; skin patches having electrodes that measure heart rate, respiration rate, galvanic skin activity; sphygmomanometers, or other devices. More information regarding biofeedback sensor devices and other information useful in the context of the invention can be found in U.S. Pat. No. 6,172,941 to Bieramperl ("Method to Generate Self-Organizing Processes in Autonomous Mechanisms and Organisms"), U.S. Pat. No. 6,402,520 to Freer ("Electroencephalograph Based Biofeedback System for Improving Learning Skills"), and U.S. Pat. No. 6,662,032 to Gavish et al., ("Interventive-Diagnostic Device"), each of which are hereby incorporated by reference herein in their entirety.

One or more biofeedback sensor devices 101 may be connected to, or situated near, subject 115 in a manner appropriate for the measurement of the particular physiological attribute desired. For example, a biofeedback sensor device designed to measure a subject's brain electrical activity may include a machine for producing an electroencephalogram (EEG), which may include multiple padded sensors. In this example, these multiple padded sensors may be placed on the scalp of subject 115. Other biofeedback sensor devices 101 may be used and their connection with subjects may be varied accordingly.

In one embodiment, one or more biofeedback sensor devices 101 may be operatively connected to or otherwise in communication with at least one computer system 103. Computer system 103 may be or include one or more servers, desktop computers, laptops, personal digital assistants (PDAs), cell phones, pagers, various wireless devices, or other computing devices having one or more processors or data processing capability.

According to an embodiment of the invention, computer system 103 may host bio-training application 107. Bio-training application 107 may comprise a computer application, an internet website, an intranet site, or other computer software application or site. System 100*a* may be operated by an operator, and administrator, or other user via bio-training application 107.

In one embodiment, bio-training application 107 may include one or more software modules 113*a*-113*n* for creating subject records; sampling/receiving subject data from a subject via biofeedback devices or other data input devices; analyzing processing subject data; creating, maintaining, and/or updating one or more rules or a priori knowledge regarding correlations between subject states, measurable subject data, and challenges to a patient; formulating one or more challenges to a subject designed to induce a specific state in the patient; presenting one or more challenges to a subject to induce a desired state; and/or for enabling other features or functions of the invention.

In particular, bio-training application 107 may comprise a sampling module 113*a*, a challenge presentation module 113*b*, a rules engine 113*c*, a recursive data analysis module 113*d*, an interactive game module 113*e*, and/or other modules 113*n* as described in greater detail below. For some purposes, not all modules may be necessary.

According to an embodiment of the invention, one or more associated databases 105*a*-105*n* may be operatively connected to computer system 103. Databases 105*a*-105*n* may be, include, or interface to, for example, an Oracle™ relational database sold commercially by Oracle Corporation. Other databases, such as Informix™, DB2 (Database 2) or other data storage or query formats, platforms, or resources such as OLAP (On Line Analytical Processing), SQL (Standard Language Query), a SAN (storage area network), Microsoft Access™ or others may also be used, incorporated, or accessed into the invention.

Databases 105*a*-105*n* may receive and store any information produced, processed, analyzed or formulated according to the embodiments described herein, including multiple patient records and the information associated therewith; one or more rules associated with rules engine 113*c*; a priori knowledge regarding state-specific correlations between challenges, measurable subject data, and subject states; or other data. Data produced externally, such as genetic or epigenetic expression/regulatory data or other experimental data useful for the operation of this invention may also be loaded and stored on one or more databases 105*a*-105*n*.

A bio-training system according to the invention (e.g., bio-training system 100*a* or 100*b*) may include one or more challenge presentation devices. As illustrated in FIG. 1A a challenge presentation device may include, for example, a data display device 109. Data display device 109 may include, for example, a computer monitor, television monitor, liquid crystal display screen, or other data display device. Other challenge presentation devices may include a sound emitting device (e.g., speaker), vibration device, electrode, or other device capable of presenting challenges to a subject.

A bio-training system according to the invention (e.g., bio-training system 100*a* or 100*b*) may include one or more data input devices. As biofeedback sensor devices (e.g., biofeedback sensor device 101) sample subject data that is then input into computer system 103, the biofeedback sensor devices may be considered data input devices. However, other data input devices 111 may be utilized in addition to or instead of the biofeedback sensor devices.

Data input devices 111 may also sample/receive subject data and may be operatively connected to or otherwise in communication with computer system 103. Data input device 111 may include, for instance, a keyboard, a mouse, an alphanumeric keypad, a touch screen, a voice recognition device (e.g., a microphone and accompanying software), a camera or other optical device, or other device capable of receiving voluntary or involuntary input from subject 115. In some embodiments, data input devices 111 may not only be used to gather subject data but may also be used to receive input/commands from one or more operators or administrators. In some embodiments, there may be multiple data input devices 111, some of which are specifically designated for sampling subject data and others that are designated for operator/administrator interaction with the bio-training system.

Figure 1B:
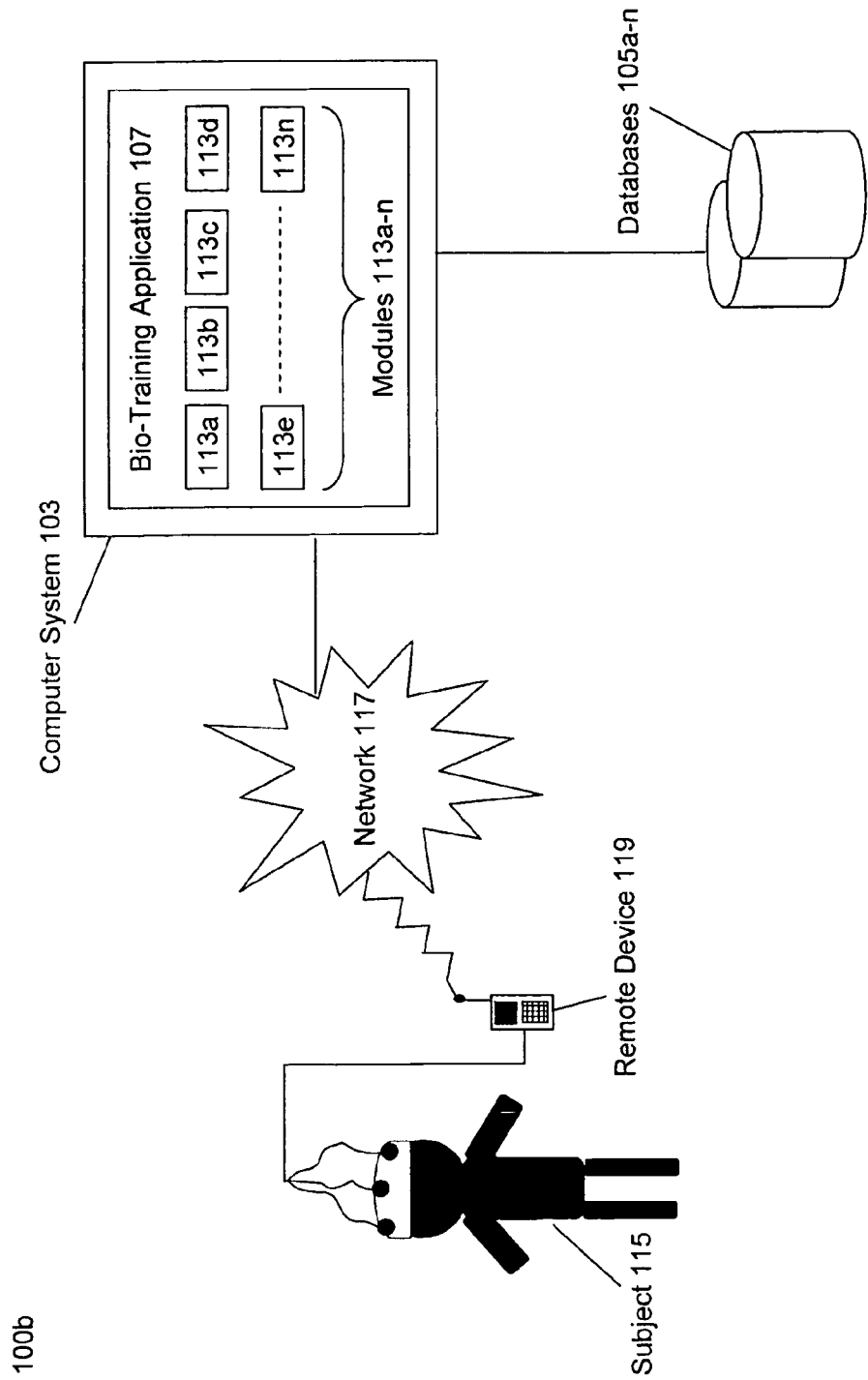
FIG. 1B illustrates a schematic diagram of a bio-training system according to an embodiment of the invention.

According to another embodiment of the invention illustrated in FIG. 1B, a system 100*b* is provided for a remote-enabled bio-training system. Remote-enabled bio-training system 100*b* may include, inter alia, a computer network 117 and a remote device 119. Remote device 119 may include a laptop computer, a personal computer, a cell phone, a personal digital assistant (PDA), a computer gaming system, a personal/portable gaming system, or other remote (e.g., remote from computer system 103, an administrator, a clinical setting, etc.) or wireless-remote computing device. Remote device 119 may be capable of receiving, recording, and/or transmitting information between subject 115 and computer system 103, or any part of a bio-training system over computer network 117. In one embodiment, some or all of the components of the bio-training system may utilize short-range wireless technology (e.g., Bluetooth or other technology) to enable real-time conveyance of data within the system. In other embodiments, long-range wireless technology (e.g., cellular, RF, or other technology) may be used. The use of a remote device may allow interaction between a subject and a bio-training system away from a clinical setting, for instance, in the home, in the workplace, on the street, or other setting.

Remote device 119 may include various hardware/software/firmware enabling multiple functions. For instance, remote device 119 may serve as any combination or subset of, for example, biofeedback sensor device 101, data display device 109 (or other challenge presentation device), data input device 111, database 105, computer system 103, or other elements. Furthermore, in some embodiments, remote device 119 may store, load, and/or operate bio-training application 107 and some or all of its modules.

Those having skill in the art will appreciate that the invention described herein may work with various system configurations. Accordingly, more or less of the aforementioned system components may be used and/or combined in various embodiments. It should also be understood that various software modules 113a-113n utilized to accomplish the functionalities described herein may be maintained on one or more of biofeedback sensor device 101, data input device 111, challenge presentation device (e.g., data display device 109), remote device 119, or other components of systems 100a and 100b, as necessary. In other embodiments, as would be appreciated, the functionalities described herein may be implemented in various combinations of hardware and/or firmware, in addition to, or instead of, software.

Figure 2:
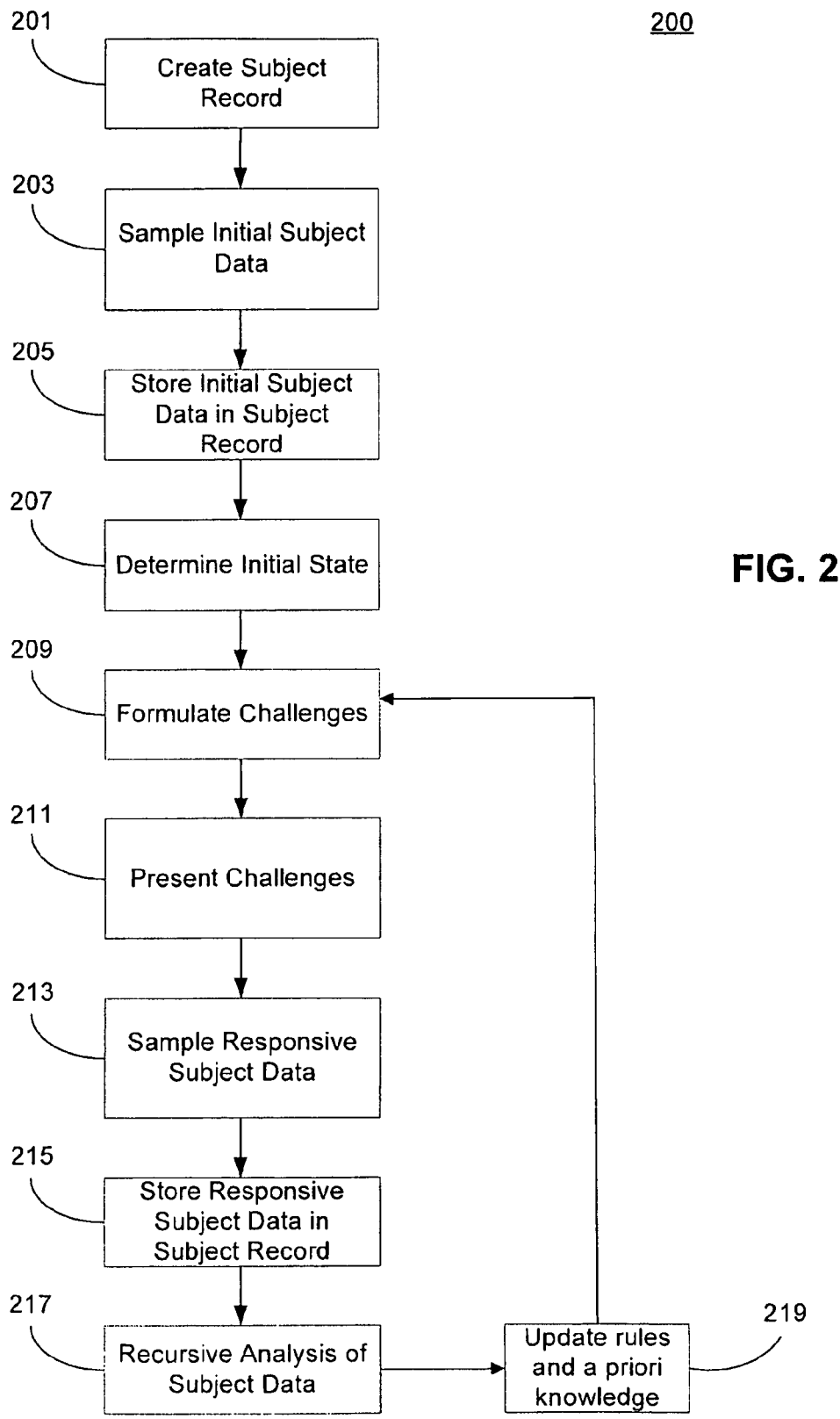
FIG. 2 illustrates a flowchart of a method according to an embodiment of the invention.

FIG. 2 illustrates a process 200, that enables the identification, modeling, and modulation of evocable bio-controllers of global regulatory network functions to induce changes in the state of a subject. Process 200 may utilize a bio-training system (e.g., bio-training system 100a or 100b) to gather data regarding subject states and their correlation to certain measurable subject data (including genetic and epigenetic expression data) and challenges that induce changes in such states.

In one embodiment, process 200 may include an operation 201 wherein a subject record may be created. In one embodiment, the record may be created using a data management module, which may be one of the modules 113a-113n of bio-training application 107. In one example, wherein the subject is a human being (e.g., subject 115), the subject record may include identifying information regarding the subject (e.g., name, address, social security number, or other identifying information), characteristic information regarding the subject (e.g., age, ethnic background, weight, height, or other characteristics), medical history of the subject, current pathology or symptoms of the subject (if any), and/or other information. The patient record may also include experimental data. As discussed below, this experimental data may include: data regarding the subject's interaction with the bio-training system (e.g., type/characteristics of challenges presented to the subject, the date/time the challenges were presented to the subject, patient response to challenges, or other data), sampled subject data (this data may include data gathered in response to challenges or initial/baseline subject data), any interpretation of sampled subject data (e.g., the specific-state indicated by any set or subset of sampled subject data), comments on the experimental data, or other information.

In an operation 203, baseline/initial subject data may be sampled. In one embodiment, the subject data sampled by the bio-training system (whether initial subject data, responsive subject data, or other subject data) may include four categories of data related to a subject: 1) biophysical properties, 2) voluntary action, 3) involuntary action, and 4) genetic and epigenetic expression data. In other embodiments, other types of subject data may be used in the invention. Biophysical properties, as described above, may include physiological attributes, or other measurable biological characteristics of a subject. Voluntary actions as subject data may be sampled using the one or more data input devices (e.g., data input devices 111) of the bio-training system. In one example, voluntary action subject data may include responses to questions, interaction with games or puzzles, or may include other voluntary actions. In one example, involuntary actions as subject data may include observations regarding body language, facial muscle status, eye movement, or other observable or measurable involuntary indicators and may also be input into the bio-training system using one or more data input devices 111.

Genetic or epigenetic expression data as subject data may refer to sampled data indicative of gene transcription (e.g., DNA to mRNA) or molecular regulation thereof, gene translation (e.g., mRNA to amino acid) or molecular regulation thereof, other gene regulatory action in a subject. Genetic or epigenetic expression data may be obtained using known clinical and molecular biological laboratory techniques. For example, if information regarding the expression of a certain gene in a tissue sample is desired, a sample of the tissue may be taken, the cells comprising the tissue sample may be lysed, the mRNA from the cells may be isolated, primers annealing to mRNAs of the gene of interest and reverse transcriptase may be introduced to the isolated mRNA, PCR may be performed to produce cDNA's of the mRNA's in the sample representing a transcribed gene of interest, and the presence/magnitude of the cDNA's may be measured using microarray visualization techniques (or other techniques). Other molecular laboratory procedures may also be used for numerous reasons (e.g., the presence of an mRNA may not always be indicative of actual protein production—transcription is not always indicative of translation). For more information regarding molecular biological measurement techniques, see *Current Protocols in Molecular Biology*, Vol. 4, (Frederick M. Ausubel et al. eds.), John Wiley & Sons, Inc. (1999), which is hereby incorporated by reference herein in its entirety (see particularly Section 22.2, "Preparation of mRNA for Expression Monitoring).

The use of conventional molecular biological laboratory techniques to obtain genetic or epigenetic subject data may involve a lag time between sampling of subject cells and the production of actual genetic or epigenetic subject data useful with the bio-training system. However, heretofore unrealized techniques for faster genetic or epigenetic expression data production may be used with the invention when developed, including those capable of measuring gene expression data in real-time or close to real-time. Additionally, genetic or epigenetic data as subject data may include extrapolations of probable genetic or epigenetic expression based on known or predicted correlations between contemporaneously measurable subject data (e.g., biophysical properties, voluntary action, involuntary action, etc.) and genetic or epigenetic expression. Furthermore, as mentioned herein, the bio-training system itself may be used to enhance ability of researchers to make such correlations between subject data measurable in real time and gene or epigenetic expression.

Sampling of subject data (whether initial subject data, responsive subject data, or other subject data) may be enabled by sampling module 113a of bio-training application. Sampling module 113a may enable interactivity between any biofeedback sensor devices, input devices, data entry software (e.g., which may be utilized to input genetic/epigenetic expression data or other data originating from outside the bio-training system), or other source and the one or more databases 105a-105n or other parts of the bio-training system. This interactivity may enable sampling/receiving subject data and/or other data from the aforementioned devices, programs, or data sources for use with the systems and methods of the invention.

In an operation 205, the baseline data may then be stored in a database (e.g., database 105) as part of the subject's record.

In one embodiment the baseline/initial subject data sampled in operation 203 may be relatable to one or more states that are being investigated using the bio-training system (e.g., if certain brain activity is relatable to the presence, absence, degree, or other characteristic of a state that exhibits attention deficit hyperactivity disorder, that brain activity may be monitored). As such, the baseline/initial subject data may be used to determine an initial state of the subject in an operation 207.

In some embodiments, the initial state may likely be already known and the sampling of initial subject data may serve to create a subject data profile of that state. For example, genetic and/or epigenetic expression data may be sampled as subject data in an operation 203 to give a baseline of the genetic/epigenetic expression profile of the initial state determined in operation 207. While genetic/epigenetic expression data may be the best indicator of a subject's state, other subject data may be more easily measurable in real time. As such, other types of subject data may also be sampled to determine their baseline profiles. Contemporaneously measurable subject data (e.g., that other than other than genetic/epigenetic data) may be correlated to certain genetic/epigenetic profiles using known relationships. As such, the change in a contemporaneously measurable set of subject data may be used to extrapolate to certain genetic/epigenetic profiles. In other embodiments, the bio-training system may be used to establish those applicable correlations by sampling of both contemporaneously measurable subject data, and genetic/epigenetic data at each interval of the iterative process described herein.

In one embodiment, determining a state of the patient (including the initial state or subsequent states) may include determining the functional capacities of the subject. By way of example, if the state of the patient were relatable to the neurological system of the subject, the neurological functional capacities may include attention, concentration, temporal-sequential ordering ability, spatial ordering, memory, language, neuro-motor functions, social cognition, higher order cognition or other neurological capacities. In this example, these neurological capacities may be determined largely using voluntary action data gathered from the patient during interaction with puzzles, games, or other activities. Additionally, in this example, the baseline functional capacity data of the subject may be utilized to express the current state of the subject as a neuro-developmental construct. A neuro-developmental construct as used herein may include a model of an individual patient's neurological profile in addition to any other pertinent profiles. An example of neuro-developmental constructs may include one or more models of the roles or neurological functions of a human brain. These roles need to be coordinated, integrated and synchronized for certain development, achievement, and/or other proper functionality. The construct may be utilized as the iterative process of the invention progresses to model subsequent states of the subject and/or to test or represent the relationships between state changes, measurable patient data, and challenges presented to the subject.

Different neurological functions may be used or emphasized during different tasks or stages in a person's life. For example, the roles of different neurological functions change when a high school student switches from a math test to a game of tennis. These neurological functions may also interact in "harmony" with one another to enable the human brain to perform the various tasks necessary for human life. Other types of functions may also need to interact and/or be emphasized in other systems). When a human exhibits pathological symptoms that may be neuro-developmental in origin, an investigation into the one or more neurological functions that are not performing properly may be an appropriate starting point to discerning what is wrong and how to fix it. The bio-training system's profiling of these functional capacities and development of neuro-developmental constructs performs and/or aids this investigation. In other embodiments, other functional capacities and other constructs of other aspects of the subject may be determined using subject data and used in the invention.

In an operation 209, one or more challenges may be formulated for presentation to the subject. In one embodiment, these one or more challenges may be formulated by rules engine 113c. In one embodiment, rules engine 113c may include or access a priori knowledge relating to what types/characteristics of challenges may be useful in changing the state of the subject from the initial state to a desired state—e.g., a self-organizing state (or if the specifics of the desired state is as of yet unknown, simply shifting the subject out of the initial state towards other states). As such, rules engine 113c may utilize some or all of the sampled subject data from operation 203. In some embodiments, rules engine 113c may be completely automatic in its application of rules/a priori knowledge. In other embodiments, manual interaction of an operator, administrator, or other human interaction may be utilized by rules engine in formulating challenges and/or building rules/a priori knowledge.

In some embodiments, there may be little or no a priori knowledge regarding what challenges to administer. In these embodiments, the iterative process described herein (e.g., process 200) may cycle through a plurality of iterations to build up correlations between the types/characteristics of challenges, measurable subject data (including genetic/epigenetic data) and specific shifts in state. Indeed the recursive analysis functions of the invention are themselves targeted towards uncovering state-specific controllers that enable the development of challenges that shift subjects from specific symptomatic states to specific self-organizing asymptomatic states.

In an operation 211, the one or more formulated challenges may be presented to the subject. As mentioned above, the types/characteristics of challenges may be varied depending on the a priori knowledge correlating measurable subject data (including genetic/epigenetic data), challenges, and specific states. Examples of types of challenges may include interactive puzzles and games (including videogames and/or games playable on game consoles, mobile phones, or other gaming or electronic devices, but also include non-video enabled games) or other visual or interactive stimuli. Other types of challenges may include auditory components (e.g., sounds, words, instructions, any of which may be administered either alone or in conjunction with the aforementioned interactive games or in conjunction with other challenges), tactile stimuli, olfactory or taste stimuli, electrical stimuli, and/or other stimuli. In some embodiments, a challenge may include any stimuli, interaction, or event that is intended to induce a change in subject state (or at least a change in measurable subject data—genetic/epigenetic data included)

In one embodiment, the challenges of the bio-training system may utilize an "internal" stimulus, instruction, or event intended to evoke a subject's self-organizing influences. For example, an instruction prompting a subject to focus awareness on the subject's own breath may be administered. Other internal stimuli or stimuli intended to evoke a subject's self organizing influences may be used as they become more sustainable via the strategies of the learning reinforcement module. Subject focus on or continuous administration of an internal stimulus, instruction, or event may continue as functional capacity data, oscillatory influence data, functional regulatory pathway data, cell-cycle trajectory data, and/or other data may be sampled/profiled by the bio-training system. Furthermore, additional bio-adaptive challenges may be introduced before, during, or after subject focus on an internal stimulus. Continued subject focus on an internal stimulus may serve to aid in the identification, modeling, and manipulation of bio-controllers and self-organizing influences and may aid in evoking autonomous optimization of state-specific neuro-developmental operation.

By the inclusion of a myriad of possible environmental influences, the bio-training system may incorporate artificial life (AL) designs to refine the search for evocable constraints within any given environmental context. The bio-controller dynamics evoked by a combination of interactivity and environmental challenges may include self-organizing influences that trigger optimized neuro-developmental operation of a subject. Such optimized state-specific neuro-developmental operation may shift the subject into an asymptomatic state in the same manner as the use of beta blockers in cardiovascular health.

The self-organizing influences evoked by the bio-training system that may result in subject state change may include "global self-organizing influences." Global self-organizing influences may include information regarding self-organizing bio-controllers found in or applicable across numerous species (see discussion herein regarding use of the bio-training system with plant and non-human animal like systems).

In some embodiments, the one or more challenges may be presented to the subject using challenge presentation devices (e.g., data display devices, speakers, electrodes, or other devices). In these embodiments, challenge presentation module 113b may facilitate the presentation of such challenges. For example, challenge presentation module 113b may provide interactivity between computer system 103/bio-training application 107 and the challenge presentation devices, such that the challenges formulated by the rules engine are successfully presented to the patient. In some embodiments, where an operator or administrator is charged with presenting a challenge to the patient, challenge presentation module 113b may provide instructions to the operator or administrator as to the specifics of presentation of the challenge.

Presentation of the one or more challenges to the subject may evoke self-organizing influences, and may induce optimized neuro-developmental operation and asymptomatic states of presence. These results may be an expected or desired result of the specific design of the challenges (e.g., due to a robust set of rules/a priori knowledge) or may be an experimental byproduct that is used in further iterations to investigate/elucidate bio-controller knowledge/correlations. In some embodiments, induction into optimized state-specific self-organizing neuro-developmental operation may be incremental (as mentioned above, changes from initial state to desired state may be incremental) and/or temporary.

After or during the presentation of the one or more challenges in operation 211, responsive subject response data may be sampled in an operation 213. Similar to the baseline/initial subject data, the subject data sampled from the subject in operation 213 may include any of the four defined categories of data. The type of responsive subject data sampled in operation 213 may be data that is known (e.g., in the a priori knowledge) to be relatable the desired state (e.g., the responsive subject data is relatable to one or more pathologies or symptoms that are being investigated using the bio-training system). In some embodiments, the type of response data sampled may be of the same type as the baseline/initial subject data of operation 203 (e.g., to study how the response data differs from the baseline data). In other embodiments, the type of data sampled may be different.

In an operation 215, the response data may be stored in the database as part of the subject's record. In an operation 217, the response data may be analyzed. This analysis may be performed by recursive analysis module 113d and, as mentioned above, may include a comparison of the responsive subject data to the initial subject data (in later iterations of the iterative process, this comparison may include comparing the most current set of responsive data to some or all of previous responsive subject data and the initial subject data). This analysis may also identify an effect that the one or more challenges of operation 211 had on the state of the subject (e.g., positive, negative, state change detected but not necessarily positive or negative, no effect), and/or any incremental measurements of said effect (e.g., slight movement towards desired state, great movement toward desired state, etc.). Using this analysis of the differences in the responsive subject data to previous subject data, the type/characteristics of challenges used, and the effect on the state of the subject, the recursive analysis module may update rules engine 113c and the a priori knowledge to reflect what was learned in the previous sample-challenge-sample iteration. These updates may be saved in database 105 in an operation 219.

Process 200 may then return to operation 209 to formulate additional challenges based on the updated rules engine 113c and a priori knowledge. Thus, process 200 may be cycle through any number of iterations to produce an ever-deepening data store. As mentioned above this data store may include genetic/epigenetic expression data and correlations of this expression data to contemporaneously measurable subject data (e.g., biophysical properties, voluntary actions, involuntary actions, or other contemporaneously measurable data) that is indicative of specific states, and to the types/characteristics of challenges that produce changes in these specific states. Thus, the ever-deepening data store uncovers state-specific controllers that can be used to purposefully shift subjects from habituated pathological states to self-organizing non-habituated asymptomatic states.

Figure 3:
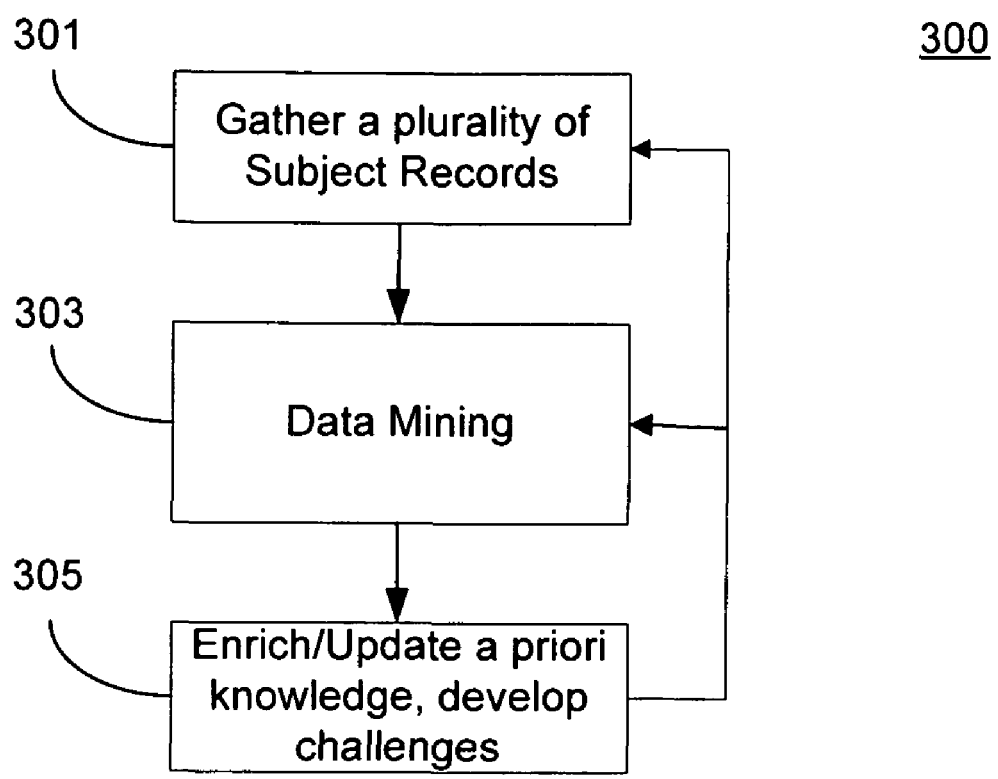
FIG. 3 illustrates a flowchart of a method according to an embodiment of the invention.

FIG. 3 illustrates a process 300, wherein data regarding multiple subjects may be utilized to further elucidate state-specific controlling influences that shift subjects from habituated pathological states to self-organizing asymptomatic biological states. In an operation 301, a plurality of subject records that include experimental data may be gathered or produced (e.g., using iterative analysis of process 200) and saved in a database 105.

In some embodiments, because specific states are being investigated, only subjects with the same or similar initial states (e.g., the same pathological conditions/symptoms) may be gathered/stored. In other embodiments, the correlation between the grouped subject records may be looser, especially when investigating less-characterized pathologies.

In an operation 303, one or more data mining techniques may be applied to the some or all of the plurality of subject records. In some embodiments, recursive analysis module 113d may perform this data mining operation. Mining data across multiple subject records may provide enhanced statistical probability of uncovering meaningful globally applicable correlations and may provide a robustness in the resultant correlations.

Data mining operation 303 may seek to elucidate the challenges that best drive subjects towards a specific desired state (e.g., a specific self-organizing state). Data mining operation 303 may also seek to elucidate the measurable subject data (including genetic/epigenetic data) that best reflects a specific state (whether that state be an undesirable pathological state, a desirable asymptomatic state, or in between). Furthermore, data mining operation 303 may also seek to elucidate correlations between contemporaneously measurable subject data (e.g., biophysical properties, voluntary action, involuntary action, etc.) and genetic/epigenetic expression data. Generally, data mining operation 303 may correlate challenges (e.g., type/characteristics of), measurable subject data (including genetic/epigenetic expression data), and specific states. In some embodiments the existing rules/a priori knowledge of rules engine 113c may be used as a basis for this data mining. In other embodiments where little to no a priori knowledge exists about the aforementioned correlations, data mining across a plurality of patient records may be used to build the rules/a priori knowledge.

The correlations uncovered by operation 303 may have produced a greater understanding of certain state-specific biological controlling influences, i.e., bio-controllers (in the form of the aforementioned correlations between subject data, challenges, and specific states). In an operation 305, this understanding of these bio-controllers may be used to enrich the a priori knowledge used in an iterative process such as process 200 and may aid in formulating challenges that successfully shift individual subjects from habituated pathological states to self-organizing asymptomatic states by meaningful degrees. As illustrated in FIG. 3, process 300 may then return to operation 303 for further data mining using the enriched rules/a priori knowledge or may return to operation 301 to gather additional subject records prior to further data mining (thus, process 300, like process 200, may be an iterative process).

The recursive analysis performed in an operation 217 during iterative cycling of process 200, the data mining operation performed in operation 303 of process 300, and/or other analysis performed by recursive analysis module 113d may iteratively analyze (e.g., fractal statistical analysis) data resulting from continued sampling of subject data (an ever-expanding data store) to formulate specific types and levels of bio-adaptive challenges for presentation back to the subject. Recursive analysis/data mining may include multi-logic and multi-analytical processes, which may integrate conventional statistical measures with appropriate non-linear dynamic rule based functional pattern analyses. As part of this analysis, an iterative data mining method may be used to "drill" down beneath conventional surface stimulus-response constraints of data. Recursive analysis/data mining may subject data to many different statistical screens including, but not limited to, stochastic models, multi-fractal models, and/or other statistical screens.

Furthermore, rules engine 113c may incorporate artificial intelligence (AI) and other machine-learning methods that draw and "learn" from recursive data analysis module 113d to design appropriate levels/types of bio-adaptive challenge. This aspect of the bio-training system may utilize functional capacity data and other data, with the goal of identifying, modeling and exploring for the evocable bio-controllers of global regulatory network functions.

As mentioned above, the subject need not be a human being. Some investigation into the bio-controllers of genetic/epigenetic expression using the bio-training system may involve plants and/or animal systems. This enables researchers to take samples cells of all types of subject tissues, including those of vital organs, to measure the expression in tissues that may be most prevalent in state change (this access might not be viable for human patients). As described herein, the correlation of evolutionarily conserved gene families may be used to relate the states of plants or animal systems to the states of human beings. Thus, investigation of plant or animal systems using the invention may be quite beneficial in enhancing the rules/a priori knowledge that are later used with human subjects. In addition, as described herein, the use of the iterative process of the bio-training system on virtual systems/simulations may also be useful in enhancing the rules/a priori knowledge that are ultimately used with human subjects.

Figure 4:
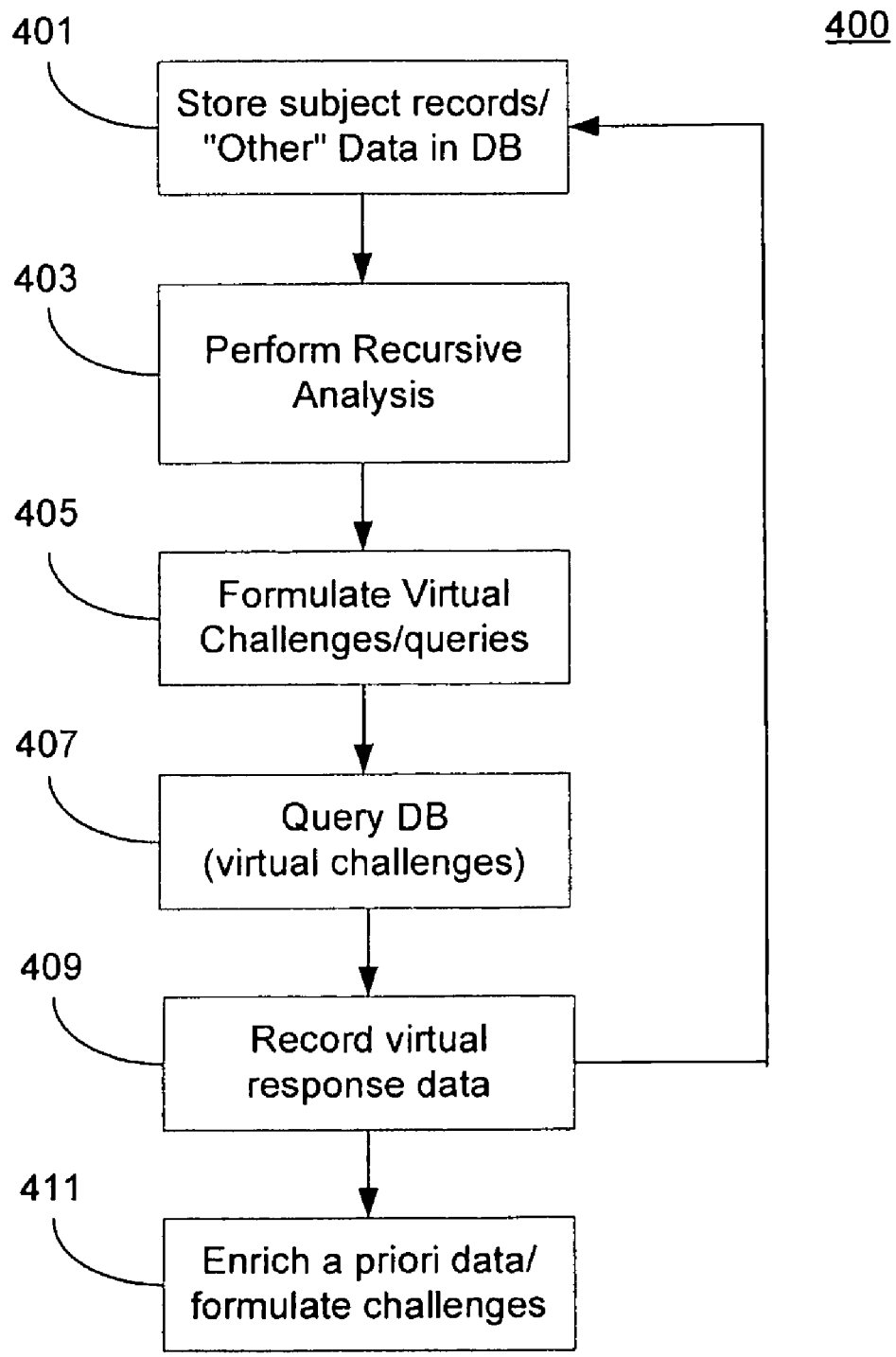
FIG. 4 illustrates a flowchart of a method according to an embodiment of the invention.

FIG. 4 illustrates an exemplary process 400, wherein a bio-training system (e.g., bio-training system 100a or 100b) may challenge virtual/simulated biological systems to enable the identification of bio-controllers to induce optimized global state-specific mediated neuro-developmental operation. Process 400 utilizes virtual challenges/queries to a simulated biological system which may also elucidate correlations between subject data (including genetic/epigenetic expression), challenges, and specific subject states. In an operation 401, multiple subject records including experimental data, functional capacity data, neuro-developmental constructs, gene and epigenetic regulatory network data, and/or other data (collectively, the "self-organizing data set") may be produced or collected using process 200 and/or other processes and stored in one or more databases. The self-organizing data set need not originate from within a bio-training system, but may originate from outside sources.

In some embodiments, the self-organizing data set may be used to construct a virtual central nervous system, virtual gene regulatory network, or other virtual biological system. Such virtual systems may be established and maintained within a bio-training system by a virtual system module of the bio-training application. This virtual biological system may be operating in a self-organizing/asymptomatic state such that queries to it elucidate characteristics of specific asymptomatic states; it may be operating at a symptomatic state to demonstrate the characteristics of habituated pathological states; and/or it may transition from one state to another to demonstrate the specifics of such a transition.

In an operation 403, recursive data analysis module 113d may perform recursive analysis on the self-organizing data set and/or its virtual biological system. In an operation 405, rules engine 113c module may formulate one or more virtual challenges/queries to the virtual system of the self-organizing data set. In some instances, the queries of process 400 may be analogized to the challenges of process 200 (e.g., the challenges of process 200 may be thought of a "queries" to the biological network/system that makes up a living subject). In an operation 407 the virtual challenges/queries may be presented to the virtual system/self-organizing data set. The one or more challenges/queries presented in operation 305 may be designed to elucidate correlative data regarding measurable subject data (including genetic/epigenetic expression data) challenges, states, cell-regulatory pathways, bio-controllers, self-organizing influences, and other data relevant to the processes, systems, and state-specific goals described herein.

In an operation 409, results virtual challenge/queries of operation 407 may be recorded and stored in one or more databases. These results may then be input back into the self-organizing data set and used to further develop the understanding of the virtual biological system, which may be used for the formulation of additional queries/virtual challenges forming a "virtual iterative loop" similar to those described in process 200. In an operation 411, this ever-deepening iterative analysis may elucidate complex information associated with functional regulatory pathways, bio-controllers, and state-specific self-organizing influences, which may be added to the rules/a priori knowledge of the correlation between challenges, states, subject data, bio-regulatory networks and their influences, etc. used in processes 200 and 300. This further addition to the rules/a priori knowledge may be used to further formulate challenges that successfully transition subjects from pathological to asymptomatic self-organizing states.

In one embodiment, the bio-training system may also include a genetic analysis module containing search engine capabilities that use layers of gene and evolutionary algorithmic functions similar to a Genetic Network Analyzer (GNA) to uncover additional information relevant to the identification, modeling, and modulation of state-specific bio-controllers. The information sought by the genetic analysis module may include genetic and epigenetic expression (e.g., subject data) data that may be used to confirm that an alteration in self-organizing expression has occurred. Network analysis may include a method of, inter alia, verifying transcriptional expression within a known network expression model. The genetic analysis module, similar to the Genetic Network Analyzer, may include or interface with a computer-implemented system for the modeling and simulation of gene and protein regulation processes on a molecular level. Information produced by a genetic analysis module may be utilized by the recursive analysis performed by recursive analysis module 113d and thus may be introduced into the interactive processes of the bio-training system to refine and support identification, modeling, and modulation of bio-controllers and evocable state-specific self-organizing influences (e.g., processes 200, 300, or 400).

In one embodiment, through continuous interaction with a bio-training system, a subject's global adaptive control cell-cycle trajectories may be profiled for environmental sensitivities that demonstrate bi-directional responsiveness to, and, where applicable, contribute to self-organizing influences. Cell-cycle trajectories may include the molecular cascade of changes a cell undergoes in coordination with other cells and their environments. Cell-cycle trajectory information be utilized in the recursive analysis of recursive analysis module 113d and thus may be introduced into processes for the identification, modeling, and modulation (e.g., processes 200, 300, or 400) of bio-controllers and evocable state-specific self-organizing influences.

In one embodiment, a bio-training system may include an embedded learning reinforcement module that is part of bio-training application 107. This learning reinforcement module may include artificial intelligence (AI), artificial life (AL) or other adaptive/machine-learning routines. The learning reinforcement module may operate similar to an Iterative Group Analysis (iGA), may "learn" from a subject, and may continuously redesign itself. For example, a learning reinforcement module may maintain, by various rewarding reinforcements for the subject (e.g., access to the next level of an interactive game supported by the bio-training system) precise load-to-performance ratios on any actual, virtual, or emerging self-organizing influence trajectory produced by iterative sampling, challenging, or querying (real or virtual). A learning reinforcement module may draw on emerging patterns from iterative/continuous biofeedback profiling or challenges to a subject (e.g., challenges to a living subject's central nervous system [CNS] or virtual challenges or queries to a database or virtual subject) to implement any redesign or "learning" from individual subjects or emerging data. This evolving design of a bio-training system may allow the bio-training system (e.g., it may be part of or may inform recursive analysis module 113d) to better identify and model mechanisms within complex biological systems that prove so often to be elusive "moving targets" (such as bio-controllers). This evolving design may be implemented by recursive analysis module 113d and rules engine 113c in processes (such as processes 200, 300, and 400) that utilize continuous iterative sampling, challenging, or querying (real or virtual).

The learning reinforcement module enlists motivated subject involvement by incorporating various rewarding reinforcements for the subject such as, for example, access to the next level of an interactive game supported by the bio-training system, prizes, or other rewarding reinforcements. This reinforcement may sustain subject participation during "non-entertaining" intervals when the AI/AL precision of load-to-performance ratios are increased on an actual, virtual, or emerging self-organizing influence trajectories as indicated or produced by iterative sampling, challenging, or querying (real or virtual).

In one embodiment, a learning reinforcement module may measure and map modes of oscillatory influence. Oscillatory influences may include, but are not limited to, a molecular target's availability to interactive strategies that optimize synchronization and/or asynchronization potentials of a subject's cellular communications across macro and molecular co-expression bio-pathways. As used herein, a target may include a particular target gene or group of genes, a particular target protein or group of proteins, a target chemical reaction/interaction or group of thereof (e.g., a cascade of reactions/interaction), or other targets. These synchronization potentials may include the ability of cellular groups to synchronize their activity through chemical communication. Uncovering these synchronization potentials may be relevant to influencing the state of a subject in that multiple cellular groups may need altering for complete and/or more sustained state change. As synchronization potentials and other dynamic cell-signal potentials are clarified, a learning reinforcement module may utilize an interactive domain of a bio-training system to adapt so as to address additional functional targets.

The learning reinforcement module may also search for global oscillation patterns that may exist across species or across living systems. Information produced by a learning reinforcement module may be introduced into processes for the identification, modeling, and modulation (e.g., processes 200, 300, or 400) of bio-controllers and evocable state-specific self-organizing influences.

In one embodiment of the invention, molecular biological laboratory measurement techniques may be used to gather or verify gene expression data regarding various states. This gene expression data may include, among other things, data regarding cell regulatory networks or chemical cell signaling cascades. Gene expression data may also include "orthologue" data. As used herein, "orthologues" may refer to sets of co-expressed genes that are evolutionarily conserved across different organisms. Molecular measurement techniques used in this type of investigation may include southern blot, northern blot, microarray analysis, combinatorial high throughput or ultra-high throughput molecular measurements, or any method of measuring chemical cellular communication. Functional brain imagery may also be used to gather and verify information regarding the chemical communication and gene expression profiles of states.

In one embodiment, a bio-training system may also include an interactive game module 113e that may include software enabling presentation of an interactive game to a subject. An interactive game presented to the subject may include a video game, an action/graphic-based game, a text-based game, and/or other type of game. An interactive game may facilitate the supraliminal or subliminal presentation of challenges, instructions, or stimuli to a subject as well as a the reception of responses/data from the subject. In some embodiments, the interactive game may operate alongside and/or utilize one or more biofeedback sensor devices.

In one embodiment, an interactive game may be presented to the subject via a data display device. A data display device may include a computer monitor (as a part of a computer or other computer-implemented system), a television, an LCD screen, a speaker, or other device capable of presenting data to a subject. Additional components may be necessary for processing data and receiving data from a subject in conjunction with an interactive game. In other embodiments, an interactive game may be presented to a subject via a remote device such as, for example, remote device 119 of FIG. 1B.

In one embodiment, the bio-training system may also include modules for receiving, processing, and/or utilizing video/audio/photo/dvd examples of artistic and physically expressive disciplines, athletic, martial, yogic, and/or therapeutic trainings, inclusive of all entertainment/artistic media formats. These received media may enable a subject using the bio-training system of the invention to sample, and, where appropriate, layer these media into different versions of biofeedback formats of the system's interactivities for greater personalization, and ultimately, optimized engaging functionality. In some embodiments, there may be processes for the skillful transition from sampling to purchase where there exist proprietary interests.

In one embodiment, the invention may provide for a novel computer chip design/firmware module for uploading distributed biofeedback data from several source points on a subject using, for example, wearable sensor ensembles mounted to the subject (e.g., a human subject). The novel chip design/firmware module may also provide for the integration of other multicasting media though a wireless device. The chip/firmware module may also include uploading and downloading capacities for the inclusion of biofeedback processes. Additionally the chip design/firmware module may enable downloading video/audio/photo/dvd examples of artistic and physically expressive disciplines, athletic, yogic, and therapeutic trainings, inclusive of all entertainment/artistic media formats onto the bio-training system. As mentioned herein, these uploaded media enable a subject of the bio-training system to sample them and, where appropriate, layer these media into versions of biofeedback formats of the systems interactivities for greater personalization and optimized engaging functionality.

Figure 5:
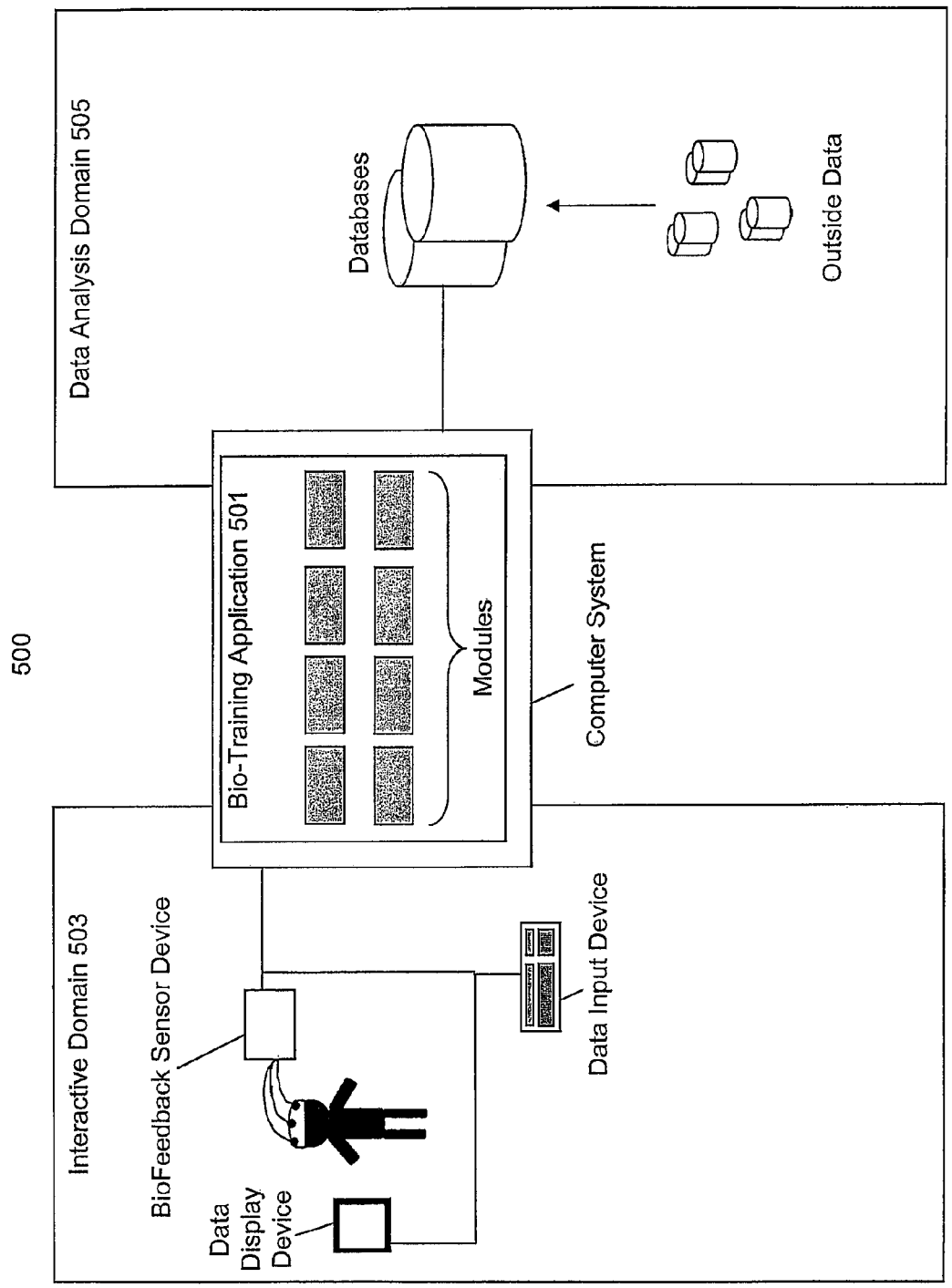
FIG. 5 illustrates a diagram of the two primary functional domains of a bio-training system according to an embodiment of the invention.

FIG. 5 illustrates an exemplary system 500, a bio-training system according to an embodiment of the invention. System 500 may include a bio-training application 501 that may be used for the integration of two primary functional domains of a bio-training system according to the invention. Bio-training application 501 may operate according to a specific methodology known as "state, specific learning memory and behaviors" (SSLMB). A domain 503 of system 500 illustrates the first primary functional domain of a bio-training system. Domain 503 may primarily deal with the subject interactivity of system 500. This interactivity may include formulating and presenting challenges, stimuli, instructions, or other data to a subject and sampling or receiving subject data. Other interactivity may be included within domain 503.

A domain 505 illustrates the second primary functional domain of a bio-training system. Domain 505 may primarily be a data analysis domain. Data analysis may include, for example, recursive data analysis as applied throughout the systems and methods described herein. Data analysis may also include the profiling and processing of data to identify, model, and modulate, bio-controllers and state-specific self-organizing influences. Data profiled and/or processed may include, for example, cell-cycle trajectories, functional regulatory pathways and other data as well as formulation of challenges and queries (both virtual and real).

SSLMB may utilize a convergence of virtual challenges to data (the data analysis domain) and actual challenges and profiling of a subject's central nervous system (CNS) (the interactive domain) as described in processes 200, 300, and 400. This convergence of domains, the analysis of data produced in both domains (including recursive analysis, administration of real and virtual challenges and queries, the evolution of methods via a learning reinforcement module, and other elements of the system), and the wealth and complexity of information brought with it may be useful in precisely clarifying networked clusters of bio-controllers that are sensitive to the state of presence and associated targeted adjustments within individual subjects and groups of subjects. Thus, SSLMB may combine data from both real and virtual challenges to identify the functional constraints of the subject-systems regulatory states in real-time. SSLMB may also clarify globally applicable bio-controller modeling information.

With the novel convergence of interactivities and "state" methodologies, the bio-training system explores the global networked controller influences that shape formative inter and intra-relationships of "state," environmental, gene, and epigenetic performance influences. With the additional inclusion of bioinstrumentation such as, for example, femtosecond lasers, attosecond lasers, or other lasers or instrumentation, the bio-training system enables exploration of quantum controllers that may function in non-local contributions to regulatory networks and feed appropriate biofeedback data into the training designs of the system. As these lawful roles are clarified, the present system identifies and models gene-targeted phenotypic cellular pathways that give the greatest indication of capacity for amplification. The synergy of interaction and "state of presence" explores mechanisms of action and models of control such as, for example, hierarchy, heterarchy, and holarchy, that contribute to transition thresholds. These transition thresholds articulate evolutionarily conserved global regulatory cell-signaling bio-capacities/bio-controllers. From the elucidated bio-controllers, the system may explore how these lawful capacities can be engaged to cooperatively to further induce and recruit those "states," brain regions, and distributed network influences that support the emergence of adaptations indicating enhanced and/or optimized functionality and performance.

In one embodiment, the bio-training system supports the identification, modeling, and modulation of regulatory bio-controllers for the unique subject to induce rapid optimized autonomous (effortless) learning-integration potentials for performance. The introduction of these learning-integration potentials may be achieved via the novel data analysis and actual/virtual querying of the bio-training system. Rapid access of effortless learning integration and "automaticity" (effortless) is made possible by the precision and hardiness of global entrainments at the state-specific levels of attention, focus, and presence brought about by the system.

It is well known in biosemiotic and neuroscience research that the nervous system uses various conditioning strategies to entrain, generalize, and habituate functional processes in a relatively accurate fashion. This co-evolutionary bio-training system incorporates its methodologies to meet these inherent strategies and the natural states that are required to mediate Nature's conditioning processes for the purposes of measurable refinements. These measurable refinements are indicated by increased performance variables that may be demonstrated first, within the regulatory constraints of the system itself, e.g., optimized transcription. The bio-training system skillfully accesses these inherent evolutionary bioprocesses. The global self-organizing core of such lawful regenerative bio-function is focused on in a variety of ways, as stated above. A most central method of the bio-training system's focusing approach is to "search," in this instance, for regenerative self-organizing controller functions, elucidated by the various domains of the invention, that naturally operate in nature's "patterning" of adaptive strategies. The bio-training then supports state-specific entrainment integration of up-regulated processes, identified by the system and methods of the invention, by aligning with Nature's conditioning rules so as to more readily achieve broader brain generalization of such identified global readiness states. These optimized global readiness states can be measurably confirmed by the lawful, and most deeply conserved, evolutionary regenerative measures; self-organizing transcriptional enhancers.

As the understanding of the map of the human genome increases, the number of identified potential drug targets also increases. As such, practical research must shift towards validating viable gene targets, rather than simply identifying potential targets. Concurrently, RNA interference technology has demonstrated success in interacting with valid drug targets to successfully treat disease by silencing pathological genes. However, a greater magnitude of potential of RNA interference technology may lie in the ability to silence expression of a single allele of a single gene at the lowest possible RNAi dose. This potential may rely on a deeper understanding of the molecular machinery of RNA interference machinery. RNA interference may be used with various state-specific learning memory and behavior (SSLMB) technologies to validate efficacy outcomes of certain genetic (or other) targets.

While the specification discusses changes from pathological states to asymptomatic states, the invention may also be utilized to transition subjects from states characterized by learning limitations to those of optimal adaptive learning, from those of suboptimal readiness for any number of life challenges to optimal readiness/awareness, and/or from any suboptimal state to a more optimal state.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A computer-implemented system for inducing or more deeply integrating a change of state in a subject, comprising:

at least one data input device configured to sample initial subject data, at a first time, the initial subject data including at least genetic or epigenetic expression data indicative of an initial state of the subject;

a data storage device configured to store the initial subject data as part of a subject record associated with the subject;

one or more processing devices configured to:
determine at a rules engine, based on at least a subset of information stored in the subject record, one or more challenges to be presented to the subject that, at least partially, manipulate one or more bio-regulatory controllers; and a challenge presentation device configured to present the one or more challenges to the subject at a second time, wherein the one or more challenges include one or more of visual stimuli, tactile stimuli, olfactory stimuli, auditory stimuli, or electrical stimuli, wherein the at least one data input device is further configured to sample, at a third time, responsive subject data that is responsive to the one or more challenges, the responsive subject data including at least genetic or epigenetic expression data indicting a response by the subject to the one or more challenges, and wherein the data storage device is further configured to store a record of the one or more challenges and the responsive subject data as part of the subject record, wherein the one or more processors are further configured to:
determine, from at least the initial subject data and the responsive subject data, whether the one or more bio-regulatory controllers have been manipulated by the one or more challenges so as to invoke at least one self-organizing mechanism in the subject that influences a transition from the initial state to a desired state, update the rules engine based on the determination, and determine, at the updated rules engine, one or more additional challenges that further manipulate the one or more bio-regulatory controllers to further invoke the at least one self-organizing mechanism to further influence the transition from the initial state to the desired state, wherein the challenge presentation device is further configured to present the one or more additional challenges to the subject at a fourth time.

2. The system of claim 1, wherein the desired state is a measurably more self-organized state than the initial state.

3. The system of claim 1, wherein the one or more challenges and the one or more additional challenges manipulate the one or more bio-regulatory controllers to invoke state-specific genetic and epigenetic expression within the subject that changes the state of the subject from the initial state to the desired state, the desired state being measurably more self-organized than the initial state.

4. The system of claim 1, further comprising a plurality of additional subject records stored in the data storage device, at least one of the additional subject records relating to a different subject, wherein the one or more processors of the rules engine are further configured to utilize at least a subset of the plurality of additional subject records to determine the one or more challenges and the one or more additional challenges.

5. The system of claim 4, wherein the at least a subset of the plurality of additional subject records relates to one or more of a plant organism or a group of plant organisms.

6. The system of claim 1, further comprising a plurality of additional subject records stored in the data storage device, at least one of the additional subject records relating to a different subject, wherein the one or more processors are further configured to utilize at least a subset of the plurality of additional subject records to update the rules engine.

7. The system of claim 1, wherein the subject is one of a human being, a plurality of human beings, a non-human animal, a plurality of non-human animals, a plant organism, a group of plant organisms, or a simulated biological system.

8. The system of claim 1, wherein the at least one data input device comprises one or more of a biofeedback sensor device, a keyboard, a mouse, an alphanumeric keypad, a touch screen, or a voice recognition device.

9. The system of claim 1, wherein one or more of the initial subject data and the responsive subject data further comprise one or more of biophysical property data, voluntary action data, or involuntary action data.

10. The system of claim 1, wherein one or more of the initial subject data and the responsive subject data further comprise biophysical property data and wherein biophysical property data includes one or more of brainwave activity, galvanic skin activity, blood pressure, pulse rate, blood gas, body temperature, or functional brain attributes.

11. The system of claim 1, wherein one or more of the one or more additional challenges include one or more of visual stimuli, tactile stimuli, olfactory stimuli, auditory stimuli, or electrical stimuli.

12. The system of claim 1, wherein one or more of the one or more challenges and the one or more additional challenges are presented to the subject via an interactive videogame.

13. The system of claim 1, wherein the challenge presentation device includes one or more of a computer monitor, a television monitor, a speaker, or an electrical stimulation device.

14. The system of claim 1, wherein the subject record includes one or more timestamps indicating:
a time and date that initial subject data was sampled,
a time and date that the one or more challenges were presented to the patient, or,
a time and date that responsive subject data was sampled.

15. A computer-implemented method for inducing or more deeply integrating a change of state in a subject, comprising:
sampling, by at least one data input device, initial subject data at a first time, the initial subject data including at least genetic or epigenetic expression data indicative of an initial state of the subject;
storing, in at least one memory device, the initial subject data indicative of a subject record associated with the subject;
determining, at one or more processing devices providing a rules engine and based on at least a subset of information stored in the subject record, one or more challenges to be presented to the subject that, at least partially, manipulate one or more bio-regulatory controllers, wherein the one or more challenges include one or more of visual stimuli, tactile stimuli, olfactory stimuli, auditory stimuli, or electrical stimuli;
presenting, by at least one challenge presentation device, the one or more challenges to the subject at a second time;
sampling, by the at least one data input device, at a third time, responsive subject data that is responsive to the one or more challenges, the responsive subject data including at least genetic or epigenetic expression data indicting a response by the subject to the one or more challenges;
storing, in the at least one memory device, a record of the one or more challenges and the responsive subject data as part of the subject record; and
determining, at the one or more processors, from at least the initial subject data and the responsive subject data, whether the one or more bio-regulatory controllers have been manipulated by the one or more challenges so as to invoke at least one self-organizing mechanism in the subject that influences a transition from the initial state to a desired state;
updating, by the one or more processors, the rules engine based on the determination;
determining, by the one or more processors providing the updated rules engine, one or more additional challenges that further manipulate the one or more bio-regulatory controllers to further invoke the at least one self-organizing mechanism to further influence the transition from the initial state to the desired state; and
presenting, by at least one challenge presentation device, the one or more additional challenges to the subject at a fourth time.

16. The method of claim 15, wherein the desired state is a measurably more self-organized state than the initial state.

17. The method of claim 15, further comprising repeating, in an iterative fashion, for a plurality of iterations, the steps of:
sampling of responsive subject data by the at least one data input device,
storing, in the at least one memory device, a record of the one or more challenges and the responsive subject data,
analyzing, by the one or more processors, changes in the response subject data from the initial subject data, wherein the initial subject data includes the initial subject data and any responsive data obtained prior to the most recent responsive subject data,
updating, by the one or more processors, the rules engine according to the analyzed changes, and
determining, by the one or more processors, one or more additional challenges.

18. The method of claim 17, further comprising:
performing the iterative repetition of steps for one or more additional subject to produce a plurality of subject records;
analyzing, at the one or more processors, the plurality of subject records to determine the characteristics of challenges that are most likely to invoke the at least one self-organizing mechanism in the subject that influences a change of state from the initial state to the desired state.

19. The method of claim 15, wherein one or more of the one or more challenges and the one or more additional challenges manipulate the one or more bio-regulatory controllers to invoke state-specific genetic and epigenetic expression within the subject that changes the state of the subject from the initial state to the desired state, wherein the desired state is measurably more self-organized than the initial state.

20. The method of claim 15, wherein the subject is one of a human being, a plurality of human beings, a non-human animal, a plurality of non-human animals, a plant organism, a group of plant organisms, or a simulated biological system.

21. The method of claim 15, wherein one or more of initial subject data and responsive subject data are sampled by one or more of a biofeedback sensor device, a keyboard, a mouse, an alphanumeric keypad, a touch screen, or a voice recognition device.

22. The method of claim 15, wherein one or more of the initial subject data and the responsive subject data further comprise one or more of biophysical property data, voluntary action data, or involuntary action data.

23. The method of claim 15, wherein one or more of the initial subject data and the responsive subject data further comprise biophysical property data and wherein biophysical property data includes one or more of brainwave activity, galvanic skin activity, blood pressure, pulse rate, blood gas, body temperature, or functional brain attributes.

24. The method of claim 15, wherein one or more of the one or more additional challenges include one or more of visual stimuli, tactile stimuli, olfactory stimuli, auditory stimuli, or electrical stimuli.

25. The method of claim 15, wherein one or more of the one or more challenges and the one or more additional challenges are presented to the subject via an interactive videogame.

26. The method of claim 15, wherein the at least one challenge presentation device that presents one or more of the one or more challenges or the one or more additional challenges to the subject include one or more of a computer monitor, a television monitor, a speaker, or an electrical stimulation device.

27. The method of claim 15, wherein the subject record includes one or more timestamps indicating:

a time and date that initial subject data was sampled, a time and date that the one or more challenges were presented to the patient, or, a time and date that responsive subject data was sampled.

* * * * *